United States Patent [19]

Schreuder

[11] 4,263,284
[45] Apr. 21, 1981

[54] HAND CLEANING COMPOSITION

[76] Inventor: J. C. P. Schreuder, 712 Veenbesstraat, Soest, Netherlands

[21] Appl. No.: 52,827

[22] Filed: Jun. 27, 1979

[30] Foreign Application Priority Data

Jun. 30, 1978 [NL] Netherlands .......................... 7807077

[51] Int. Cl.$^3$ ..................... A61K 7/50; A61K 31/725; C11D 3/43; C11D 3/48

[52] U.S. Cl. .................................... 424/180; 252/89.1; 252/106; 252/153; 252/162; 252/171; 252/173; 252/174.11; 252/174.15; 252/174.17; 252/174.21; 252/174.25; 252/542; 252/170; 252/172; 424/273 R

[58] Field of Search ............... 252/153, 154, 155, 142, 252/143, 162, 163, 164, 165, 166, 167, 168, 173, 174.21, 174.25, 89.1, 542, 548; 252/DIG. 5; 424/170, 172, 180, 273 R

[56] References Cited

U.S. PATENT DOCUMENTS

| | | | |
|---|---|---|---|
| 3,277,013 | 10/1966 | Gianladis | 252/153 |
| 3,941,722 | 3/1976 | Shevlin | 252/524 |
| 4,155,870 | 5/1979 | Jorgensen | 252/131 |

OTHER PUBLICATIONS

Geoghegan, J. T., et al.: "Waterless Hand Cleaners", *Soap & Chemical Specialties*, Aug. 1969, pp. 54–55, 58 & 82.

Lazorisak, N. W.: "Waterless Hand Cleaners & Barrier Creams", *Detergents & Specialties*, Apr. 1969, pp. 26, 28 & 73.

Lesser, M. A.: "Waterless Hand Cleaners", *Drug & Cosmetic Industry*, Mar. 1953, pp. 326, 327, 408–414.

*Primary Examiner*—Dennis L. Albrecht
*Attorney, Agent, or Firm*—Hammond & Littell, Weissenberger and Muserlian

[57] ABSTRACT

Skin cleaning agents comprising (A) a continuous oil phase consisting essentially of straight or branched paraffinic oils of 10 to 30 carbon atoms in the chain, (B) a dispersed aqueous emulsified phase, (C) a buffer consisting essentially of lactic acid and triethanolamine for maintaining the normal pH of the outer skin tissue layers, (D) an emulsifying system consisting essentially of mono- and diglycerides of higher natural fatty acids and ethoxylated glycerine esterified with fatty acids of the formula

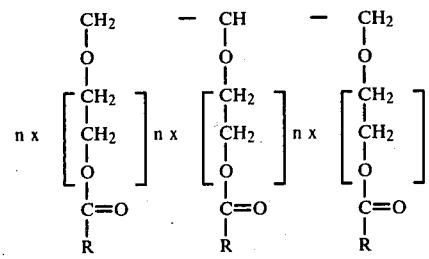

wherein n is a number between 20 to 45, and preferably between 30 and 35, the $R_s$ are individually a saturated or unsaturated fatty acid residue derived from animal or vegetable oils such as palmitic acid, lauric acid, oleic acid or linoleic acid, (E) -glycerine and (F) - caraghenates optionally modified by esterification of the sulfonic acid residues with lower alcohols.

19 Claims, No Drawings

HAND CLEANING COMPOSITION

STATE OF THE ART

Various compositions have been proposed in the last few decades for easy and efficient cleaning of skin, particularly hands which are often and chronically exposed to filth from industrial and technical processes but none of them have been completely satisfactory. The problem with known oil-in-water emulsions wherein an oil or fat phase is dispersed in an aqueous phase is that the cleaning agent did not clean the filth sufficiently. The problem with known water-in-oil emulsions was that they were not sufficiently stable because of unsuitable emulsifier systems.

Another problem with known cleaning systems was the necessity to wash the filth away from water whereby the natural occuring protective elements of the skin tissue were regularly washed away also which after prolonged use results in one or more serious affections of the skin such as dermatitis or dermatose. Therefore, there is still a growing need for skin cleaning agents for regular use to remove filth or soil from the skin caused by a wide variety of soiling such as use of paints, lacquers, glues, adhesives, printing inks, metal compositions, rusty metal accessories such as in automobiles, cement and the like or by regular contact with germ contaminated materials.

OBJECTS OF THE INVENTION

It is an object of the invention to provide novel skin cleaning compositions which can be used frequently without injury to the skin.

It is another object of the invention to provide a novel method of removing a wide variety of soil from the skin.

These and other objects and advantages of the invention will become obvious from the following detailed description.

THE INVENTION

The novel skin cleaning agents of the invention are comprised of (A) a continuous oil phase consisting essentially of straight or branched paraffinic oils of 10 to 30 carbon atoms in the chain, (B) a dispersed aqueous emulsified phase, (C) a buffer consisting essentially of lactic acid and triethanolamine for maintaining the normal pH of the outer skin tissues layers, (D) an emulsifying system consisting essentially of mono- and diglycerides of higher natural fatty acids and ethoxylated glycerine esterified with fatty acids of the formula

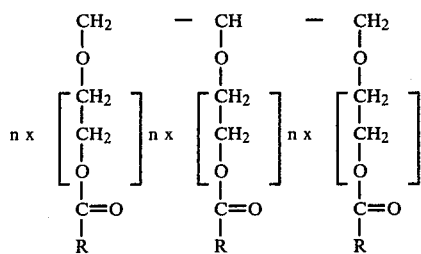

wherein n is a number between 20 and 45, and preferably between 30 and 35, the Rs are individually a saturated or unsaturated fatty acid residue derived from animal or vegetable oils such as palmitic acid, lauric acid, oleic acid or linoleic acid, (E)-glycerine and (F)-caraghenates optionally modified by esterification of the sulfonic acid residues with lower alcohols.

The continuous oil phase consists of straight or branched chain paraffinic oil fractions of 10 to 30 carbon atoms, preferably 12 to 25 carbon atoms and have a boiling range of 140° to 400° C. and a viscosity up to 35 centistokes at 25° C. The compositions contain 20 to 60%, preferably 25 to 40% by weight of the said phase.

The buffer of the composition is essentially a mixture of lactic acid and triethanolamine to maintain the normal pH of the outer skin tissue layers, namely about 5 to 6. The lactic acid, preferably the naturally occuring L(+) optical isomer, is used in amounts of 0.1 to 1.5%, preferably about 1%, of the weight of the total composition and triethanolamine is used in amounts of 1 to 2%, preferably about 1.5%, by weight of the total composition and the buffer system has been found to be suitable for supplementing or temporarily replacing outer skin layers.

The emulsifying system consists mainly of mono- and diglycerides of the higher natural fatty acids, such as linoleic acid, oleic acid, palmitic acid, lauric acid or combinations thereof and ethoxylated glycerine esterified with fatty acids of the formula

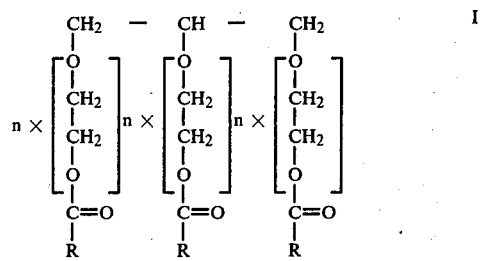

wherein n is a number between 20 and 45, preferably between 30 and 35 and R is a saturated or unsaturated fatty acid residue derived from animal or vegetable oils such as palmitic acid, lauric acid, oleic acid or linoleic acid, whereby R may be the same or different fatty acid residues in one molecule, but preferably the same (e.g. Tagat TO ®).

In contrast to a large number of of other similar systems which were used for this purpose, the emulsifying system surprisingly appears to meet very well the requirement, stipulating that not too large amounts of the decidedly indispensable emulsifying agents may be used with reference to occurring skin irritations, as only relatively small amounts appear to be necessary as compared with those amounts of known systems, while the emulsifying system of the present invention may be regarded as especially affable to the skin, which feature is connected with a relatively low hydrophilic-lipophilic balance value. It will be appreciated that the emulsifying agents of the mono- and diglyceride type optionally may be replaced by other similar emulsifying components.

The ratio between the amount of the mono- and diglycerides and the ethoxylated triglycerides of formula I may vary, while the advantageous characteristics are obtained from 10 to 100 parts of mono- and diglycerides per part of ethoxylated triglyceride and preferably about 25 parts of the mono- and diglycerides per part of ethoxylated triglycerides. The total percentage by weight of the beforementioned emulsifying system, calculated on the weight of the total system may vary from 1-5% but will preferably be about 3% by weight for the most optimal results.

It will be appreciated that the present amount of the emulsifying agent is significantly smaller than the amount used in known emulsifying systems, namely about five times smaller which is an important and actual advantage of this emulsifying system.

Glycerine, which acts as a stabilizer of the emulsion, is present from 0.5 to 5.0%, preferably up to about 2% by weight of the total composition. The experimentally found attractive results may be explained by assuming an additional function of glycerine, which might consist of a moisture regulating action, optionally in interaction with the lactic acid-triethanolamine combination which also might cause an additional advantageous effect.

The caraghenates, i.e. polysaccharides bearing a sulfonic acid residue are preferably those of natural origin such as those derived from seaweed suitable for that purpose. The sulfonic acid residues may optionally be esterified with lower alcohols such as glycol, propylene glycol and glycerol (modified caraghenates). Such caraghenates appear to effect a surprisingly attractive stabilizing and film forming effect of the total system to be applied on the skin, while as an additional advantageous effect, the known attractive properties of these caraghenates such as elimination of an eventual hardening of sore tissue and the resulting healing thereof without or with less extensive scars, as well as the advantageous healing effect and the complex forming properties with proteins and/or metal ions, appear to be maintained in the final total system.

In connection therewith, the cleaning effect is also strongly improved due to the easier elimination of e.g. polluting undesired metal ions in a complexed state. It appears that the caraghenates have to be present in an amount from 0.1 to 2% by weight, calculated on the weight of the total system and preferably up to about 1.0%.

Moreover in addition to the indicated basic components, some additional secondary components may be added to obtain the most optimal results, such as e.g., allantoin which facilitates healing of the skin which is known from prior art, and up to a content of 0.1 to 2% by weight, calculated on the weight of the total system and preferably up to about 0.2% is used, and additional stabilizers such as, for example, systems consisting of montmorillonites, the free oxygen sites of which are occupied by quaternary groups. Examples of such systems, which are preferably used in the composition are e.g. the so called Bentones ® and Propaloids ® up to a content of from 0.7 to 2% by weight, calculated on the weight of the total system and preferably to about 1.0%.

Now it was surprisingly found that in the compositions of the invention with relatively low concentrations of these quaternary modified montmorillonites, no separation of one or more of the components occurs and particularly not in the relatively low viscous systems which are preferably used for practical reasons.

Lower alkanol may be added for a fast gelation of the quaternary montmorillonites. The alkanol may be added in an amount of from 0.1 to 1% by weight of the total composition and preferably in an amount of half the amount of the montmorillonites.

For special applications, e.g. in cases of intensive dirtiness, an abrasive such as quartz powder and silver-sand and preferably silver-sand may be added up to an amount of 5% by weight, preferably 2 to 2.5% by weight, of the total compositions.

Preservatives such as esters of p-hydroxybenzoic acid, and for instance NIPAGEN ® and NIPASOL ® may also be added up to an amount of from 0.02 to 0.08% by weight, calculated on the total weight, preferably about 0.05% by weight with reference to the total weight, and up to a content in the aqueous phase of from 0.05 to 0.2% by weight and preferably about 0.1%, calculated on the total system. Preferably, the propyl ester of p-hydroxybenzoic acid is added to the oil phase and the methyl ester of p-hydroxybenzoic acid is added to the aqueous phase.

An unexpected advantageous effect was found in that the composition of basic ingredients is much less sensitive to growth of bacteria and molds, so that significantly smaller amounts of preservative are sufficient as compared with those in usual oil-in-water emulsions.

Silicone oils, preferably with a viscosity of $\geq 100$ cps, may be added for their dirt repelling properties as known from literature with reference to which the filthiness of the outer skin tissue is occurring less fast. The silicone oils are added up to a content of about 0.5 to 3% by weight, preferably 1.5%, calculated on the total weight of the mixture. Also, small amounts of antioxidants up to an amount of 0.01 to 0.3% may be added as well as perfumes in an amount of from 0.03 to 0.3% by weight and desinfectants such as hexachlorophene or Irgasan DP 300 in an amount up to 1.5% by weight.

Compared with known hand washing agents for the removal of filthiness from a variety of industrial sources, the present compositions are characterized by a relatively low viscosity and high stability at both high and low temperatures, and show the following significant practical advantages: The skin tissue generally remains in a better condition as essential outer skin ingredients are not regularly washed away with water. Little or no chance of dermatitis with prolonged use and no irritation due to the selected environmentally affable ingredients.

For the use of the present composition, no water is needed which results in many situations a practical advantage due to non-availability of water. Fast and efficient cleaning action caused by the dissolving power of the oil phase for a lot of pollutants such as paints, glues, and the like for which have a direct contact with the outer skin tissue and which penetrates as if it were under the dirt. Only small amounts are necessary for obtaining the desired effect. For example, about 200 sufficient cleanings of intensively filthy hands are possible per liter of the present compositions.

The hand washing compositions of the invention may be prepared by known methods for such preparations, whereby however the sequence of the addition and the amounts of the respective ingredients and, for example, also the temperatures are important.

The said handwashing creams may, for example, be prepared by gelation of e.g. the montmorillonite fraction in the oil phase to which the emulsifying agent has previously been added at a temperature of 50° to 70° C., preferably 55° to 65° C., optionally with the addition of a lower alkanol up to an amount of at most half of the weight of the montmorillonite fraction e.g. Bentones ® followed by dissolving the preservative and optionally one or more of the antioxidants are dissolved into the resulting dispersion, whereby the preservative and/or the antioxidants eventually may also be added to a previous stage. The term "lower alkanol" means an alkanol having 1 to 4 carbon atoms.

If desired, the resulting mixture is cooled to a temperature of preferably 40° C., whereafter silicon oil may also be added in a previous stage of the process. All the other ingredients (glycerine, lactic acid, triethanolamine, allantoin, caraghenates, methyl ester of p-hydroxybenzoic acid) are dissolved into the aqueous phase whereafter the mixture optionally may be cooled to a temperature of 35° to 40° C. The phases are thoroughly mixed with a stirrer for 10 to 30 minutes, preferably 20 minutes, and are subsequently homogenized until a size of the dispersed particles <5μ and preferably <3μ is reached whereafter the optional abrasive such as silver-sand may be added with thorough stirring.

It will be appreciated, that the present process is surprisingly characterized by a striking simplicity in contrast to those of most known water-in-oil emulsions, most of which could only be homogenized by means of rolling. Moreover the present process may be regarded as saving labor and energy which means a decrease of the cost. The treatment of filthy skin with the hand washing compositions of the invention is one of the features of the invention. Such a treatment is preferably carried out by the application of a small amount of the composition in an amount of from 2 to 10 ml, preferably about 6 ml, on the concerned skin followed by thorough rubbing in. The time range is dependent on the type of filthiness whereafter the skin parts are rubbed clean and dry with a cloth or tissue. An additional advantage of such a treatment is situated in the absence of a greasy skin surface immediately after the treatment, e.g. papers or documents may be touched almost immediately after treatment.

In the following examples there are described several preferred embodiments to illustrate the invention. However, it is to be understood that the invention is not intended to be limited to the specific embodiments.

EXAMPLE 1

| COMPOSITION 1 | | |
| --- | --- | --- |
| Paraffinic oil I (Shell Ondina 15) b.p. 295-390° C. | 150 g | |
| Paraffinic oil II (Shellsol T. b.p. 176-211° C.) | 150 g | |
| Mono- and diglycerides | 20 g | |
| Ethoxylated trigylcerides | 0.2 g | oil |
| Propyl p-hydroxybenzoate | 0.5 g | phase |
| Antioxidants (2,6-di-tert.-butyl p-cresol) | 0.2 g | |
| Silicone oil 500 cps | 10 g | |
| quaternary modified (Bentones ®) montmorillonites | 8 g | |
| iso butanol | 4 g | |
| water | q.s. 1000 g | |
| glycerine | 40 g | |
| lactic acid (50%, L(+)) | 20 g | aqueous |
| triethanolamine (85%) | 20 g | phase |
| allantoin | 2 g | |
| carraghenate | 10 g | |
| methyl p-hydroxybenzoate | 1 g | |
| silver sand | 20 g | |

| COMPOSITION 2 | | |
| --- | --- | --- |
| paraffinic oil I | 500 g | |
| mono- and diglycerides | 40 g | |
| ethoxylated triglycerides (Tagat TO ®) | 4 g | oil phase |
| propyl p-hydroxybenzoate | 0.5 g | |
| antioxidants | 0.2 g | |
| silicon oil (1000 cps) | 5 g | |
| quaternary modified montmorillonites | 16 g | |
| ethanol | 4 g | |
| water | q.s. 1000 g | |
| glycerine | 20 g | |
| lactic acid (50% ((+)) | 10 g | |
| triethanolamine (85%) | 10 g | acqueous phase |
| allantoin | 2 g | |
| caraghenate | 5 g | |
| methyl p-hydroxybenzoate | 1 g | |

The said compositions were prepared as follows: The oil phase was heated to 55° to 65° C. and all components thereof were dissolved. The quaternary modified montmorillonites were then dispersed therein and subsequently gelated by addition of the lower alkanol. Then, the mixture was cooled to about 40° C.

In the aqueous phase at a temperature of 35° to 40° C., the above indicated ingredients were added one after the other in the indicated order and dissolution occured. The two phases were thoroughly mixed and the emulsion was cooled to room temperature. In addition, the mixture was homogenized, and if desired an abrasive was added with thorough stirring.

EXAMPLE 2

A handwashing composition was prepared by the process described in Example 1 and contained

| | | |
| --- | --- | --- |
| paraffinic oil I | 17% by weight | |
| paraffinic oil III (Shellsol K, b.p. 193-245° C.) | 10% | |
| mono- and diglycerides | 3% | oil phase |
| ethoxylated triglycerides | | |
| propyl p-hydroxy-benzoate | 0.05% | |
| antioxidants | 0.02% | |
| quaternary modified montmorillonities (Bentones) | 1.0% | |
| propanol | 0.5% | |
| water q.s. | 100% by weight | |
| glycerine | 2% | |
| lactic acid (50%, L(+)) | 2% (i.e. 1.0%) | aqueous phase |
| triethanolamine (85%) | 1.4% (i.e. 1.2%) | |
| allantoin | 0.2% | |
| modified caraghenate | 1% | |
| methyl p-hydroxy-benzoate | 0.1% | |
| perfume | 0.05% | |

EXAMPLE 3

A handwashing composition was prepared by the process described in Example 1 and contained

| | | |
| --- | --- | --- |
| paraffinic oil I | 15% by weight | |
| paraffinic oil II | 15% | |
| mono- and digylcerides | 2% | oil |
| ethoxylated triglycerides | 0.02% | phase |
| propyl p-hydroxybenzoate | 0.05% | |
| antioxidants | 0.02% | |
| silicon oil (500 cps) | 1% | |
| quaternary modified montmorillonites | 1.8% | |
| ethanol | 0.9% | |
| water | q.s. 100% by weight | |

| | | |
|---|---|---|
| -continued | | |
| glycerine | 4% | |
| lactic acid | 2% | |
| triethanolamine | 2% | |
| allantoin | 0.2% | aqueous phase |
| caraghenate | 1% | |
| methyl p-hydroxybenzoate | 0.1% | |
| silver sand | 2% | |
| perfume | 0.1% | |

EXAMPLE 4

A handwashing composition was prepared by the process described in Example 1 and contained

| | | |
|---|---|---|
| paraffinic oil I | 20% by weight | |
| paraffinic oil III | 18% | |
| mono- and diglycerides | 2% | oil phase |
| ethoxylated triglycerides | | |
| propyl p-hydroxybenzoate | 0.03% | |
| silicon oil (1000 cps) | 1.5% | |
| quaternary modified montmorillonites (Bentones®) | 0.8% | |
| propanol | 0.4% | |
| water | q.s. 100% by weight | |
| glycerine | 2% | |
| lactic acid (50%, L(+)) | 3% (i.e. 1.5%) | |
| triethanolamine (85%) | 2.1% (i.e. 1.8%) | |
| allantoin | 0.3% | aqueous phase |
| caraghenate | 1% | |
| methyl p-hydroxybenzoate | 0.1% | |
| perfume | 0.08% | |

EXAMPLE 5

A handwashing composition was prepared by heating with vigorous stirring about 150 g of the paraffinic oil I to 55° to 60° C. and the following oil phase components were dissolved therein; 20 g of mono- and diglycerides, 1 g of ethoxylated triglycerides, 0.2 g of antioxidant and 0.5 g of propyl p-hydroxybenzoate. Stirring was continued and 10 g of quaternary modified montmorillonites were dispersed therein and subsequently gelated, while the temperature was maintained between 55° to 65° C. Then, 180 g of paraffinic oil I were added and the mixture was cooled to about 40° C.

An aqueous phase was prepared at a temperature of 35° to 40° C. containing 40 g of glycerine, 20 g of lactic acid (50%), 20 g of triethanolamine (85%), 2 g of allantoin, 10 g of modified caraghenate and 1 g of methyl p-hydroxybenzoate in about 545 g of water by addition of all ingredients with stirring until complete dissolution. Both obtained phases were thoroughly mixed and the emulsion was cooled to room temperature. The mixture was homogenized by thorough stirring.

The use of the handwashing compositions gave rise to the following advantageous effects: Cement coated hands were well cleaned. Chrome-oxide residue residing in the pores were removed by the present composition in contrast to the known compositions. Hands soiled by repairs to a silencer were well cleaned. Scalds by the silencers occurring with these repairs seemed less severe and healed faster after cleaning with the present hand washing compositions.

Printing inks, stencil inks and paints were very well removed as were latex paints and glues. After treatment, the hands were soft and smooth and the skin was certainly not dry. Repelling of dirt was obtained and chances of infection were decreased since the natural barrier of skin fats and sweat was not completely eliminated by these compositions, but was supplemental.

Various modifications of the products of the invention may be made without departing from the spirit or scope thereof and it is to be understood that the invention is not indended to be limited only as defined in the appended claims.

We claim:

1. A skin cleaning agent comprising (A) a continuous oil phase consisting essentially of 20 to 60% by weight of the composition of straight or branched paraffinic oils of 10 to 30 carbon atoms in the chain, (B) a dispersed aqueous emulsified phase, (C) a buffer consisting essentially of lactic acid and triethanolamine for maintaining the normal pH of the outer skin tissue layers, (D) an emulsifying system consisting essentially of mono- and diglycerides of higher natural fatty acids and ethoxylated glycerine esterified with fatty acids of the formula

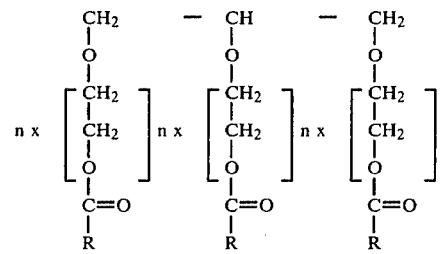

wherein n is a number between 20 to 45, the Rs are individually a saturated or unsaturated fatty acid residue derived from animal or vegetable oils, the ratio of mono- and diglycerides to ethoxylated triglycerides is 10 to 100 parts to one and are 1 to 5% by weight of the composition (E) 0.5 to 5% by weight of the composition of glycerine and (F) caraghenates optionally modified by esterification of the sulfonic acid residues with lower alcohols.

2. The composition of claim 1 wherein the stablizer is a montmorillonite with the free oxygen sites occupied by quaternary ammonium groups.

3. A composition of claim 1 also containing allantoin.

4. A composition of claim 1 wherein the paraffinic oils have 12 to 25 carbon atoms, the buffer contains 0.5 to 1.5% by weight of lactic acid and 1 to 25% by weight of triethanolamine, the caraghenates are 0.1 to 2% by weight of the composition and the alkanol is 0.1 to 1% by weight of the composition.

5. The composition of claim 4 containing 25 to 40% of the paraffinic oils, about 1% of lactic acid, about 3% by weight a mixture of 25 parts of mono- and diglycerides per part of ethoxylated triglycerides, about 2% of glycerine, about 1.0% of caraghenates.

6. A composition of claim 1 also containing 0.1 to 2% by weight of allantoin, up to 2% of Bentones, about 0.02 to 0.08% of preservative in the oil phase, about 0.05 to 0.2% of preservative in the aqueous phase, up to 3% by weight of a silicone oil with a viscosity of $\geq 100$ cps, 0.01 to 0.03% by weight of at least one antioxidant, 0.03 to 0.3% by weight of perfume and up to 1.5% by weight of a germicide disinfectant.

7. A composition of claim 1 wherein the emulsifying system (D) is comprised of mono- and diglycerides of oleic acid and ethoxylated glycerine esterified with oleic acid and n is a number of 30 to 35.

8. The composition of claim 1 containing up to 0.05% by weight of propyl p-hydroxybenzoate as an oil phase preservative and up to 0.1% by weight of methyl p-hydroxybenzoate as an aqueous phase preservative.

9. A composition of claim 1 also containing preservatives.

10. A composition of claim 1 also containing antioxidants.

11. A composition of claim 1 also containing silicone oil.

12. A composition of claim 1 also containing lower alkanols.

13. A composition of claim 1 also containing perfumes;

14. A composition of claim 1 also containing disinfectants.

15. A process for the preparation of a hand cleaning composition of claim 1 mixing at 50° to 75° C. the oil phase (A) and the emulsifying system (D) followed by optional addition of lower alkanol and then the aqueous phase (B) containing the buffer (C), glycerine (E) and caraghenates (F) at 40° C. and then stirring the resulting mixture and homogenizing the same to a dispersed particle size of $<5\mu$.

16. The process of claim 15 wherein the mixture is stirred for 10 to 30 minutes and the dispersed particle size is $<3\mu$.

17. The process of claim 15 wherein an abrasive is added with vigorous stirring.

18. A method of cleaning soiled skin which comprises rubbing the skin with an amount of a composition of claim 1 sufficient to remove soil and wiping the skin dry.

19. A method of cleaning soiled skin which comprises rubbing the skin with an amount of a composition of claim 4 sufficient to remove soil and wiping the skin dry.

* * * * *